United States Patent [19]

Aszódi et al.

[11] Patent Number: 5,075,298
[45] Date of Patent: Dec. 24, 1991

[54] CEPHALOSPORINS

[75] Inventors: József Aszódi, Choisy-le-Roi; Alain Bonnet, Livry-Gargan; Jean-François Chantot, Gressy-en-France, all of France

[73] Assignee: Roussel Uclaf, Paris, France

[21] Appl. No.: 265,252

[22] Filed: Oct. 31, 1988

[30] Foreign Application Priority Data

Nov. 3, 1987 [FR] France .................. 87-15210

[51] Int. Cl.[5] .................. C07D 501/24; A61K 31/545
[52] U.S. Cl. .................. 514/206; 540/222; 540/225
[58] Field of Search .................. 540/222, 225, 227; 514/206

[56] References Cited

FOREIGN PATENT DOCUMENTS 2157293A 10/1985 United Kingdom .

OTHER PUBLICATIONS

Chemical Abstracts vol. 112, 118535(m) (1990).
Chemical Abstracts vol. 111, 194449(g) (1989).

Primary Examiner—Nicholas S. Rizzo
Attorney, Agent, or Firm—Bierman and Muserlian

[57] ABSTRACT

A compound selected from the group consisting of a syn isomer of a compound of the formula

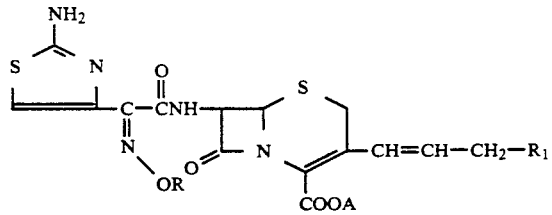

wherein R is selected from the group consisting of hydrogen, alkyl of 1 to 6 carbon atoms, alkenyl and alkynyl of 2 to 6 carbon atoms and cycloalkyl of 3 to 6 carbon atoms, all optionally substituted with at least one member of the group consisting of optionally esterified or salified carboxy, alkoxy carbonyl, carbamoyl, dimethylcarbamoyl, amino, alkylamino, dialkylamino, halogen, alkoxy and alkylthio of 1 to 4 carbon atoms, aryl, heterocyclic aryl, arylthio and heterocyclic arylthio optionally substituted by alkyl of 1 to 4 carbon atoms, $R_1$ is selected from the group consisting of

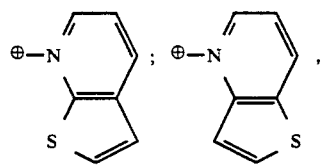

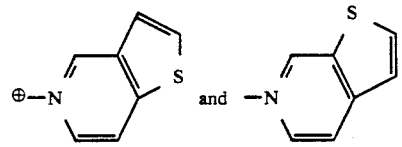

and A is selected from the group consisting of hydrogen, alkali metal, alkaline earth metal, magnesium, —NH₄ and an organic amine or A is selected from the group consisting of the residue of an easily clevable ester group or —COOA is —COO— and the wavy line indicates —CH₂—R[1] is in the E or Z position and their nontoxic, pharmaceutically acceptable acid addition salts having good antibacterial activity.

16 Claims, No Drawings

CEPHALOSPORINS

OBJECTS OF THE INVENTION

It is an object of the invention to provide the novel compounds of formula I and their non-toxic, pharmaceutically acceptable acid addition salts and their preparation and novel intermediates.

It is another object of the invention to provide novel antibacterial compositions and to provide a novel method of combatting bacterial infections in warm-blooded animals.

These and other objects and advantages of the invention will become obvious from the following detailed description.

THE INVENTION

The novel compounds of the invention are selected from the group consisting of a syn isomer of a compound of the formula

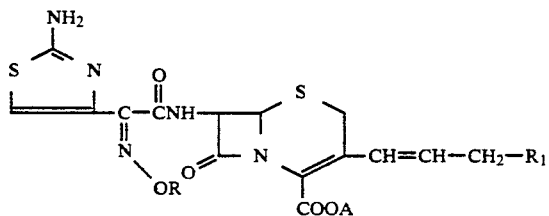

wherein R is selected from the group consisting of hydrogen, alkyl of 1 to 6 carbon atoms, alkenyl and alkynyl of 2 to 6 carbon atoms and cycloalkyl of 3 to 6 carbon atoms, all optionally substituted with at least one member of the group consisting of optionally esterified or salified carboxy, alkoxy carbonyl, carbamoyl, dimethylcarbamoyl, amino, alkylamino, dialkylamino, halogen, alkoxy and alkylthio of 1 to 4 carbon atoms, aryl, heterocyclic aryl, arylthio and heterocyclic arylthio optionally substituted by alkyl of 1 to 4 carbon atoms, $R_1$ is selected from the group consisting of

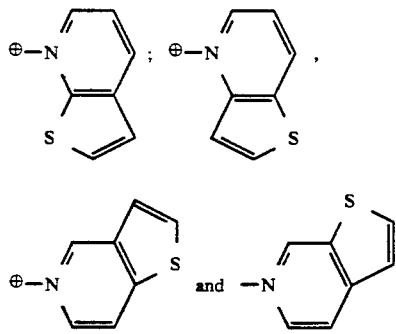

and A is selected from the group consisting of hydrogen, alkali metal, alkaline earth metal, magnesium, $-NH_4$ and an organic amine or A is selected from the group consisting of the residue of an easily cleavable ester group or $-COOA$ is $-COO^-$ and the wavy line indicates $-CH_2-R_1$ is in the E or Z position and their non-toxic, pharmaceutically acceptable acid addition salts.

Examples of alkyl of 1 to 6 carbon atoms are methyl, ethyl, n-propyl, isopropyl, n-butyl, isobutyl, tert.-butyl, pentyl, isopentyl, sec.-pentyl, tert.-pentyl, neopentyl, hexyl, isohexyl, sec.-hexyl and tert.-hexyl. Examples of alkenyl and alkynyl of 2 to 6 carbon atoms are vinyl, allyl, 1-propenyl, butenyl, pentenyl, hexenyl, ethynyl, propargyl and butynyl. Examples of cycloalkyl of 3 to 6 carbon atoms are cyclopropyl, cyclobutyl, cyclopentyl and cyclohexyl.

Examples of substituents of R groups are free carboxy; esterified or salified carboxy; alkoxycarbonyl such as methoxycarbonyl, ethoxycarbonyl; carbamoyl; dimethylcarbamoyl; amino; alkylamino such as methylamino; dialkylamino such as dimethylamino, diethylamino; halogen such as fluorine, chlorine, bromine or iodine; alkoxy such as methoxy, ethoxy or propoxy; alkylthio such as methylthio or ethylthio; aryl such as phenyl; heterocyclic aryl such as tetrazolyl; arylthio such as optionally substituted phenylthio; and heterocyclic arylthio such as tetrazolylthio and thiadiazolylthio optionally substituted with alkyl such as methyl.

Among the preferred values for R are methyl, $-CHF_2$, $-CH_2F$ and $-CH_2-COOH$. When R is alkyl, preferably methyl, it is preferably substituted with a cycloalkyl such as cyclopropyl and therefore R is also preferably cyclopropylmethyl.

Examples of A are alkali metals such as sodium, potassium or lithium; alkaline earth metals such as calcium, magnesium, $-NH_4$; and hydrogen. Examples of organic bases for A are methylamine, propylamine, trimethylamine, diethylamine, triethylamine, N,N-dimethylethanolamine, tris(hydroxymethyl) aminomethane, ethanolamine, pyridine, picoline, dicyclohexylamine, morpholine, benzylamine, procaine, lysine, arginine, histidine and N-methyl-glucamine.

Examples of easily cleavable ester groups are methoxymethyl, ethoxymethyl, isopropyloxymethyl, α-methoxyethyl, α-ethoxyethyl, methylthiomethyl, ethylthiomethyl, isopropylthiomethyl, pivaloyloxymethyl, acetoxymethyl, propionyloxymethyl, butyryloxymethyl, isobutyryloxymethyl, valeryloxymethyl, isovaleryloxymethyl, tert.-butylcarbonyloxymethyl, hexadecanoyloxymethyl, propionyloxyethyl, isovaleryloxyethyl, 1-acetyloxyethyl, 1-propionyloxyethyl, 1-butyryloxyethyl, 1-tert.-butylcarbonyloxyethyl, 1-acetyloxypropyl, 1-hexadecanoyloxyethyl, 1-propionyloxypropyl, 1-methoxycarbonyloxymethyl, 1-methoxycarbonyloxyethyl, 1-acetyloxy-butyl, 1-acetyloxyhexyl, 1-acetyloxyheptyl, phthalidyl, 5,6-dimethoxyphthalidyl, tert-butylcarbonylmethyl, allyl, 2-chloro-allyl, methoxycarbonylmethyl, benzyl or tert.-butyl.

Other residues of ester groups are methoxyethoxymethyl, dimethylaminoethyl, cyanomethyl, tert.-butoxycarbonylmethyl, 2,2-ethylidenedioxyethyl, cyanoethyl, 2,2-dimethoxyethyl, 2-chloroethoxymethyl, 2-hydroxyethoxyethyl, 2,3-epoxypropyl, 3-dimethylamino, 2-hydroxypropyl, 2-hydroxyethyl, 2-methylaminoethoxymethyl, 2-aminoethoxymethyl, 3-methoxy-2,4-thiadiazol-5-yl, 2-tetrahydropyrannyl, 1-methoxy-1-methylethyl-2-hydroxy-1-methylethyl, isopropyl; carbamylmethyl, chloromethyl, 2-chloroethyl, acetylmethyl, 2-methylthioethyl or thiocyanatomethyl.

Other residues of ester groups are 2-chloro-1-acetyloxyethyl, 2-bromo-1-acetyloxyethyl, 2-fluoro-1-acetyloxyethyl, 2-methoxy-1-acetyloxyethyl, 2-methyl-1-acetyloxypropyl, 1-methyl-1-acetyloxyethyl, 1-methoxyacetyloxyethyl, 1-acetylcarbonyloxyethyl, 1-hydroxyacetyloxyethyl, 1-formylcarbonyloxyethyl, 1-(2-thienyl)-carbonyloxyethyl, 1-(2-furyl)-carbonyloxyethyl, 1-(5-nitro-2-furyl-carbonyloxyethyl, 1-(2-pyrrolyl)carbonyloxyethyl, 1-(propionyloxycarbonyloxy)ethyl, 1-(propyloxycarbonyloxy)ethyl, 1-(isopropyloxycarbonyloxy)ethyl, 1-(methoxyethoxycarbonyloxy)ethyl, 1-allyloxycarbonyloxy)ethyl, 1-[(2,3-epoxypropyl)oxycarbonyloxy]ethyl, 1-[(2-furyl)-methoxycarbonyloxy]ethyl, 1-(2-fluoroethyl)-oxycarbonyloxyethyl, 1-(methoxycarbonyloxy)-propyl, 1-(methoxycarbonyloxy)-1-methylethyl, (methoxycarbonyloxy)chloromethyl, 1-(methoxycarboxyloxy)-2-chloroethyl, 1-(methoxycarbonyloxy)-2-methoxyethyl, 1-(methoxycarbonyloxy)allyl.

The products of formula I can also be in the form of salts of organic or mineral acids.

Examples of the acids with which the amino group or groups of the compounds of formula I can be salified are acetic acid, trifluoroacetic acid, maleic acid, tartaric acid, methanesulfonic acid, benzenesulfonic acid, p-toluenesulfonic acid, phosphoric acid, sulfuric acid, hydrochloric acid, hydrobromic acid, hydroiodic acid. The product can also be in the form of internal salts.

Among the preferred compounds of formula I are those wherein R is alkyl of 1 to 4 carbon atoms optionally substituted by at least a member chosen from free, esterified or salified carboxy, amino and halogen, as well as the products of formula I wherein $R_1$ is

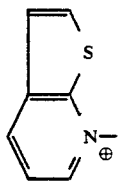

Specific preferred compounds of formula I are 7-[(E)-3-[(6R,7R) 7-[[(2-amino-4-thiazolyl) [(Z)-(methoxyimino)]-acetyl]amino]-2-carboxy-8-oxo-5-thia-1-azabicyclo[4,2,0]oct-2-en-3-yl]-2propenyl]-thieno-[2,3-b]pyridinium and 7-[(E)-3-[(6R,7R)-7[[(2-amino-4-thiazolyl) [(Z)-[(difluoromethoxy)-imino]]acetyl]amino]-2-carboxy-8-oxo-5-thia-1-azabicyclo]4,2,0]oct-2-en-3-yl]-2-propenyl]-thieno-[2,3-b]pyrdinium as well as their salts with alkali metals, alkaline earth metals, magnesium, ammonia, amino organic bases, acids, if appropriate, their internal salts and their easily cleavable esters.

It is understood that the products of formula I can exist either in the form indicated by formula I or in the form of products of the formula

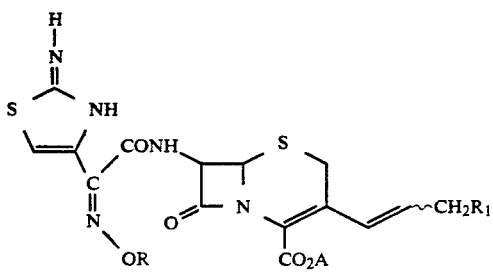

in which R, $R_1$ and A have the previous definitions.

The process of the invention for the preparation of compounds of formula I comprises reacting a reagent chosen from the reagents of the formulae

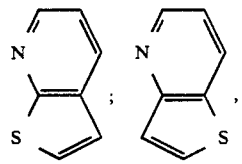

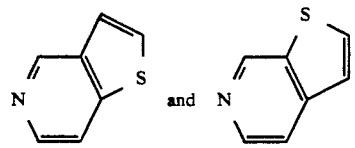

with a product of the formula

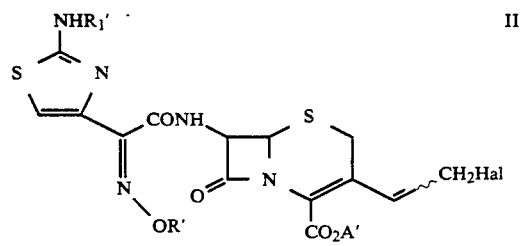

in which $R_1'$ is hydrogen or a protective group of the amino, R' is either R or a protective group of the hydroxyl, A' is hydrogen or the residue of an easily eliminated ester group and Hal is a halogen to obtain a product of the formula

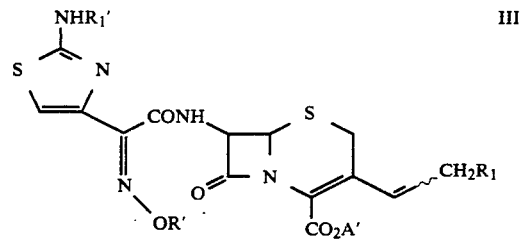

which, if desired, is separated into its E or Z isomers or the Z isomers are converted into E isomers, and the products of formula III, if appropriate, are submitted to one or more of the following reactions in any order:

a) scission by hydrolyis or by action of thiourea of all or part of the ester groups or protective groups of the amino or the hydroxyl, b) esterification or salification of the carboxyl(s) by a base, c) salification of the amino(s) by an acid.

In addition to the groups cited above, the easily cleavable ester group may be the ester formed with butyl, isobutyl, tert.-butyl, pentyl, hexyl, acetoxymethyl, propionyloxymethyl, butyryloxymethyl, valeryloxymethyl, pivaloyloxymethyl, 2-acetoxyethyl, 2-propionyloxyethyl, 2-butyryloxyethyl or 2-iodoethyl, 2,2,2-trichloroethyl, vinyl, allyl, ethynyl, propynyl, benzyl, 4-methoxybenzyl, 4-nitrobenzyl, phenethyl, trityl, diphenylmethyl, 3,4dimethoxyphenyl or phenyl, 4-chlorophenyl, tolyl, tert.-butylphenyl.

The protective group of the amino which is $R_1'$ can be for example alkyl of 1 to 6 carbon atoms such as, by preference, tert.-butyl or tert-amyl or an aliphatic, aromatic or heterocyclic acyl or a carbamoyl.

Examples are lower alkanoyl such as formyl, acetyl, propionyl, butyryl, isobutyryl, valeryl, isovaleryl, oxalyl, succinyl and pivaloyl. $R_1'$ can also be lower alkoxy or cycloalkoxycarbonyl such as for example methoxycarbonyl, ethoxycarbonyl, propoxycarbonyl, 1-cyclopropylethoxycarbonyl, isopropyloxycarbonyl, butyloxycarbonyl, tert.-butyloxycarbonyl, pentyloxycarbonyl, hexloxycarbonyl, benzoyl, toluolyl, naphthoyl, phthaloyl, mesyl, phenylacetyl or phenylpropionyl, or an aralkoxycarbonyl such as benzyloxycarbonyl.

The acyl groups can be substituted for example by chlorine, bromine, iodine or fluorine such as chloroacetyl, dichloroacetyl trichloroacetyl, bromoacetyl or trifluoroacetyl.

$R_1'$ can also be lower aralkyl such as benzyl, 4-methoxybenzyl, phenethyl, trityl, 3,4-dimethoxybenzyl or benzhydryl or haloalkyl such as trichloroethyl or chlorobenzoyl,p-nitrobenzoyl, p-tert.-butylbenzoyl, phenoxyacetyl, caprylyl, n-decanoyl, acryloyl, trichloroethoxycarbonyl or methylcarbamoyl, phenylcarbamoyl, naphthylcarbamoyl, as well as the corresponding thiocarbamoyls. The above list is not limitative and it is clear that other amine protective groups, known particularly in the chemistry of peptides, can also be used.

The protective group of the hydroxy which can be $R'$ may be an acyl such as for example formyl, acetyl, chloroacetyl, bromoacetyl, dichloroacetyl, trichloroacetyl, trifluoroacetyl, methoxyacetyl, phenoxyacetyl, benzoyl, benzoylformyl, p-nitrobenzoyl or ethoxycarbonyl, methoxycarbonyl, propoxycarbonyl, 2,2,2-trichloroethoxycarbonyl, benzyloxycarbonyl, tert.-butoxycarbonyl, 1-cyclopropylethoxycarbonyl, tetrahydropyrannyl, tertrahydrothiopyrannyl, methoxytetrahydropyrannyl, trityl, benzyl, 4-methoxybenzyl, benzhydryl, trichloroethyl, 1-methyl-1-methoxyethyl, phthaloyl.

Other acyls are propionyl, butyryl, isobutyryl, valeryl, isovaleryl, oxalyl, succinyl and pivaloyl, phenylacetyl, phenylpropionyl, mesyl, chlorobenzoyl, p-nitrobenzoyl, p-tert.-butylbenzoyl, caprylyl, acryloyl, methylcarbamoyl, phenylcarbamoyl, naphthylcarbamoyl.

In a preferred method of the process of the invention, a reagent of the formula

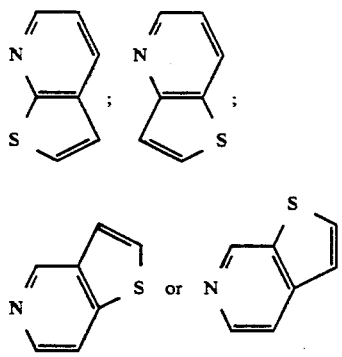

is reacted with the product of formula II under the following preferred conditions. When Hal is for example chlorine, a substitution is carried out, in situ or separately, of chlorine by an iodine in the presence of sodium iodide and then the desired reagent is added. Examples of such a reaction are described hereafter in the experimental part.

In the preparation of the products of formula III, according to the conditions employed, it is possible to obtain a mixture of E and Z isomers in variable quantities or only one isomer very predominantly, if appropriate by inversion of the configuration of the product of formula II at the time of the reaction. When a mixture of isomers is obtained, they can be separated by the usual methods, in particular by chromatography. The E isomer is obtained in very prevailing form and only this isomer is isolated in the examples According to $R_1'$, $R'$ and $A'$, the products of formula III can or cannot be the products of formula I.

The products of formula III are the products of formula I when $R'$ is hydrogen, when $R'$ is not a protective group of the the hydroxy and when $A'$ is not, amongst the easily cleavable ester groups, one of those which it is desired to eliminate.

In other cases, the aim of the action of one or more hydrolysis or hydrogenolysis agents or of thiourea on the product of formula III is to eliminate $R_1'$ when this is a protective radical of the amino, to eliminate the $R'$ when this is different from R and/or to eliminate $A'$ when this represents, amongst the easily cleavable ester groups, one of those which it is desired to eliminate. However, it is possible to eliminate $R_1'$ without affecting the substituents $R'$ and $A'$ when these must be kept. This is the case for example when $A'$ is an ester group which it is desired to keep, such as propionyloxymethyl. The nature of the reagents to be used in such a case is well known to an expert. Examples of such reactions are given further in the experimental part. For example, a description of the different methods for eliminating the various protective groups is found in French Patent Application No. 2,499,995.

The salification of the products can be carried out by the usual methods. Salification can, for example, be obtained by the action of a mineral base such as sodium or potassium hydroxide, sodium or potassium carbonate or sodium or potassium bicarbonate, on a product in acid form, or on a solvate, for example ethanol solvate or a hydrate of this acid. Salts of mineral acids such as trisodium phosphate can also be used as well as salts of organic acids.

As salts of organic acids, there can be mentioned, for example, sodium salts of linear or branched aliphatic carboxylic acids, saturated or unsaturated with 1 to 8, and preferably 2 to 10, carbon atoms. The aliphatic chains of the acids may be interrupted with at least one heteroatom such as oxygen or sulfur or be substituted by aryl such as for example phenyl, thienyl or furyl or by at least one hydroxyl or by at least one halogen such as fluorine, chlorine or bromine, preferably chlorine, by at least one lower carboxyl or alkoxycarbonyl, preferably methoxycarbonyl, ethoxycarbonyl or propyloxycarbonyl or by at least one aryloxy, preferably phenoxy. Also, aromatic acids which are sufficiently soluble can be used as organic acids, for example, benzoic acids which are substituted, preferably by lower alkyls.

Examples of such organic acids are formic acid, acrylic acid, butyric acid, adipic acid, isobutyric acid, n-caproic acid, isocaproic acid, chloropropionic acid, crotonic acid phenylacetic acid, 2-thienylacetic acid, 3-thienylacetic acid, 4-ethylphenylacetic acid, glutaric acid, the monoethyl ester of adipic acid, hexanoic acid, heptanoic acid, decanoic acid, oleic acid, stearic acid, palmitic acid, 3-hydroxypropionic acid, 3-methoxypropionic acid, 3-methylthiobutyric acid, 4-chlorobutyric acid, 4-phenylbutyric acid, 3-phenoxybutyric acid, 4-ethylbenzoic acid, and 1-propylbenzoic acid. However, one of the following is preferably used as a sodium salt: sodium acetate, sodium 2-ethylhexanoate or sodium diethylacetate.

The salification can also be obtained by the action of an organic base such as triethylamine, diethylamine, trimethylamine, propylamine, N,N-diemthylethanolamine, tris (hydroxymethyl) amino methane, methylamine, ethanolamine, pyridine, picoline, dicyclohexylamine, morpholine and benzylamine. It can also be obtained by the action of arginine, lysine, procaine, histidine, or N-methylglucamine. This salification is carried out preferably in a solvent or a mixture of solvents such as water, ether, methanol, ethanol or acetone.

The salts are obtained in amorphous or crystallized form according to the reaction conditions used. The cristallized salts are preferably prepared by reacting the free acids with one of the salts of the aliphatic carboxylic acids mentioned above, preferably, with sodium acetate. The salification of the products by mineral or organic acids in carried out by the usual conditions.

The optional esterification of the products is carried out under standard conditions. Generally, the operation is carried out by reacting the acid of formula I or a functional derivative with a derivative of the formula Z—Re in which Z is hydroxyl or halogen such as chlorine, bromine or iodine and Re is an ester group to be introduced, a list of which is given above which is not exhaustive. In some cases, it may be advantageous to carry out an esterification on a product whose amine and/or an optional oxyimino group are blocked before removing the protective group of the amine and of the oxyimino group.

The novel antibacterial compositions of the invention are comprised of an antibacterically effective amount of at least one compound of formula I and their non-toxic, pharmaceutically acceptable salts and an excipient or inert pharmaceutical carrier. The compositions may be in the form of tablets, dragees, capsules, granules, suppositories and injectable solutions.

Examples of suitable excipients are talc, gum arabic, lactose, starch, magnesium stearate, cocoa butter, aqueous and non-aqueous vehicles, fatty substances of animal or vegetable origin, paraffin, glycols, various wetting agents, dispersants and emulsifiers and preservatives. The compositions may also be in a powder to be dissolved extemporaneously in apyrogenic sterile water, for example.

The compositions have a very good antibacterial activity against gram (+) bacteria such as staphylococci, streptococci, and particularly penicillin-resistant staphylococci. Their effectivness on gram (−) bacteria, particularly on coliform bacteria, klebsiella, salmonella and proteus, is particularly remarkable.

These properties make the said products and their salts of pharmaceutically acceptable acids suitable for use as medicaments in the treatment of affections caused by sensitive germs and particularly in that of staphylococciae such as staphylococcic septicemia, malignant staphylococcia of the face or skin, pyodermia, septic or suppurating wounds, anthrax, phlegmon, erysipelas, primary or post-infuenzal acute staphylococcia, bronchopneumonia and pulmonary suppurations. These products can also be used as medicaments in the treatment of colibacillosis and associated infections, infections caused by proteus, klebsiella and salmonella and other affections caused by gram (−) bacteria.

The novel method of the invention for combatting bacterial infections in warm-blooded animals, including humans, comprises administering to warm-blooded animals an antibacterically effective amount of at least one compound of formula I and their non-toxic, pharmaceutically acceptable acid addition salts. The products may be administered topically, orally, rectally or parenterally and the usual daily dose is 3,33 to 53,3 mg/kg by oral route for the product of example 1 depending on the condition treated, the specific compound and the method of administration. The compositions may also be used to disinfect surgical instruments.

The novel intermediates of the invention are the compounds of formula III wherein $R_1'$ is an amine protective group.

Examples of suitable compounds of formula I are in the following Table wherein $R_1$, A and R have the indicated values and the 3-side chain has the indicated geometry.

| $R_1$ | A | R | isomerism $CH_2R_1$ |
|---|---|---|---|
| ⊕—N (thiazole ring) | | ⊖ $CH_2CO_2H$ | E |
| ⊕—N (thiazole ring) | | ⊖ $-\underset{CH_3}{\underset{|}{C}}-CO_2H$ with $CH_3$ | E |
| ⊕—N (thiazole ring) | | ⊖ $CH_3$ | E |
| ⊕—N (thiazole ring) | | ⊖ $CHF_2$ | E |
| ⊕—N (thiazole ring) | | ⊖ $CH_3$ | E |

| R₁ | A | R | isomerism |
|---|---|---|---|
| ⊕−N (fused pyridine-thiophene structure) | ⊖ | CHF₂ | E |
| ⊕−N (fused pyridine-thiophene structure) | ⊖ | CH₃ | E |
| ⊕−N (fused pyridine-thiophene structure) | ⊖ | CHF₂ | E |

The starting compounds of formula II are known or can be made by known methods such as described in British Patent No. 2,134,522.

In the following examples there are described several preferred embodiments to illustrate the invention. However it is to be understood that the invention is not intended to be limited to the specific embodiments.

EXAMPLE 1

7-[(E)-3-[(6R,7R)-7-[[(2-amino-4-thiazolyl)[(Z)-(methoxyimino)]-acetamido]-2-carboxy-8-oxo-5-thia-1-azabicyclo[4,2,0]oct-2-en-3-yl]-2-propenyl]-thieno-[2,3-b]pyridinium iodide

STEP A:
7-[(E)-3-[(6R,7R)-2-[(diphenylmethoxy)-carbonyl]-7-[[[(Z)-methoxyimino)][2-[(triphenylmethyl)-amino]-4-thiazolyl]acetamido]-8-oxo-5-thia-1-azabicyclo[4,2,0]oct-2-en-3-yl]-2-propenyl]thieno[2,3-b]pyridinium iodide 1.033 g of diphenylmethyl (6R,7R)-3-[(Z)-3-chloro-1-propenyl]-7-[[[(Z)-(methoxy-imino)][2-[(triphenylmethyl)amino]-4-thiazolyl]-acetamido]-8-oxo-5-thia-1-azabicyclo[4,2,0]oct-2-en-2-carboxylate and 542 mg of potassium iodide in 22 ml of anhydrous acetone were stirred for 70 minutes and the solvent was evaporated and the residue was taken up in ethyl acetate. The organic phase was washed with 0.2N sodium thiosulfate, and the solvent was dried and evaporated. 334 μl of thieno[2,3-b] pyridine and 3.2 ml of anhydrous dimethylsulfoxide were added to the residue with stirring for 75 minutes. The reaction medium was poured into water and extraction was carried out with ethyl acetate. The organic phases were washed with water, dried and evaporated to dryness and the residue was chromatographed on silica and eluted with mixtures of methylene chloride-methanol (95-5), then (92-8) to obtain 259 mg of the expected product.

| NMR Spectrum (CDCl₃ 250 MHz ppm): | |
|---|---|
| 3.70 | CH₂S |
| 4.05 | OMe |
| 5.07 | H₆ } cis |
| 5.95 | H₇ |
| 5.65 | CH₂N⁺ |
| 6.58 and 7.19 | ethylenic E Δ J 16Hz |
| 6.70 | H₅ of thiazol |
| 6.98 | COO—CH |
| 7.02–7.04 | aromatic |
| 6.87 and 7.0 | NH |
| 7.66 | H₃ |
| 8.81 | H₂ |
| 8.03 | H₅ condensed heterocycles |
| 8.81 | H₄ |
| 9.96 | H₆ |

STEP B: 7-[(E)-3-[(6R,7R)-7-[[(2-amino-4-thiazolyl)[(Z)-(methoxyimino)]acetamido]-2-carboxy-8-oxo-5-thia-1-azabicyclo[4,2,0]oct-2-en-3-yl]-2-propenyl]-thieno-[2,3-b]pyridinium iodide 150 mg of the product of Step A were dissolved in 2 ml of 66% formic acid and the mixture was heated at 70° C. for 45 minutes. The solvent was evaporated under reduced pressure and the residue was triturated with ether, filtered and rinsed with ether to obtain 94 mg of the expected product. 51 mg of the product were taken up in 0.25 ml of 66% formic acid and heated at 60° C. for 90 minutes. After cooling, 0.25 ml of demineralized water was added and the mixture was washed with ether and the aqueous solution was evaported to dryness. The residue was taken up several times with anydrous ethanol and the crystals formed were isolated and washed with ethanol by centrifuging to obtain 30 mg of the expected product.

| NMR Spectrum (DMSO 250 MHz ppm): | |
|---|---|
| 6.73 | H₅ of thiazol |
| 5.8 | H₇ (cephem, J=5Hz) |
| 5.2 | H₆ (J=16Hz = ΔE) |
| 7.12 | } ethylenic |
| 6.33 | |
| 3.67 | CH₂N⁺ |
| 9.03 | in ortho position |
| 8.14 | in meta position } of the pyridyl (t, J=8Hz) |
| 9.08 | in para position (d, J=8Hz) |
| 8.28 | in alpha position } of the thienyl |
| 7.89 | in beta position (d, J=6Hz) |

EXAMPLE 2

(6R,7R)-7-[[(2-amino-4-thiazolyl)
[(Z)]-[(difluoromethoxy)imino]]acetamido]-8-oxo-3
[(E)]
3-[7-[thieno[2,3-b]pyridino]-1-propenyl]-5-thia-1-
azabicyclo[4,2,0]oct-2-en-2-carboxylate (internal salt)

STEP A: diphenylmethyl (6R,7R)-(3-chloromethyl)-7-[[[(Z)-difluoromethoxy-imino] [2-[(triphenylmethyl)amino]-4-thiazolyl-acetamido]-8-oxo-5-thia-1-azabicyclo[4,2,0]oct-2-en-2-carboxylate 948.2 mg of diphenylmethyl (6R,7 R)-7-amino-3-(chloromethyl)-8-oxo-5-thia-1-azabicyclo[4,2,0]oct-2-en-2-carboxylate hydrochloride and 1.108 g of [difluoromethoxyimino] [2-[(triphenylmethyl)-amino-4-thiazolyl]acetic acid in 21 ml of methylene chloride were mixed together with stirring 362.3 ul of diisopropylcarbodiimide were added dropwise. Stirring was maintained for half an hour at ambient temperature and the mixture was evaported to dryness at 30° C. maximum under reduced pressure. The residue was chromatographed on silica and eluted with a methylene chloride-ethyl acetate mixture (97-3) to obtain 1.506 g of the expected product.

| NMR Spectrum (CDCl$_3$ 250 MHz ppm): | |
|---|---|
| 6.68 (s) | H$_5$ of thiazol |
| 6.78 | OC$\underline{H}$F$_2$ (t, J=72Hz) |
| 5.95 | H$_7$ (d, J=5Hz) |
| 5.10 | H$_6$ (d, J=5Hz) |
| 4.40 | —C$\underline{H}_2$—Cl (J$_A$B=12Hz) |
| 6.97 (s) | CO$_2$CH$\phi_2$ |

STEP B: [[(6R,7R)-7-[[[(Z)-[(difluoromethoxy-imino]] [(2-[(triphenylmethyl)amino]-4-thiazolyl]acetamido]-2-[(diphenylmethoxy)carbonyl]-8-oxo-5-thia-1-azabicyclo[4,2,0]oct-2-en-3-yl]methyl]triphenyl phosphonium iodide 1.467 g of the product of Step A in 20.2 ml of anhydrous methyl ethyl ketone and 1.255 g of dry sodium iodide were stirred at room temperature for one hour. After evaporation to dryness under reduced pressure at 30° C. maximum, the residue was taken up with 82 ml of ethyl acetate and the organic phase was washed with a 0.5N solution of sodium thiosulfate, then with water, and the iodine solution was dried. 915 mg of triphenyl phosphine were added all at once with stirring for 20 minutes and the mixture was evaporated to dryness under reduced pressure. The residue was triturated with 60 ml of ether and the mixture was stirred for 15 minutes and was separated to obtain 1.74 g of the expected product.

| NMR Spectrum (CDCl$_3$ 250 MHz ppm): | |
|---|---|
| 6.49 | H$_5$ of thiazol |
| 6.78 | OC$\underline{H}$F$_2$ | (t, J=72Hz) |
| 5.91 | H$_7$ | (d, d J=5 and 5Hz) |
| 5.07 | H$_6$ | (d, J=5Hz) |
| 4.46 / 5.12 | —C$\underline{H}$—P$\phi_3$ | (d, d J=5.5 and 20Hz) |
| 6.87 | CO$_2$CH$\phi_2$ | |

STEP C: Diphenylmethyl (6R,7R)-3-[(Z)-3-chloro-1-propenyl]-7-[[[(Z)-[difluoromethoxyimino]-] [2-[(triphenylmethyl)amino]-4-thiazolyl]-acetamido]-8-oxo-5-thia-1-azabicyclo[4,2,0]oct-2-en-2-carboxylate 799.6 mg of the product of Step B were added to 8.5 ml of chloroform and 5.8 ml of water and then 0.78 ml of N sodium hydroxide were added. The mixture was stirred for 5 minutes and after decanting in the presence of sodium chloride, the aqueous phases were extracted with chloroform. The combined organic phases were washed with water, dried and filtered off. Some magnesium sulfate and 0.51 ml of a 50–55% aqueous solution of chloroacetaldehyde were added to the filtrate followed by stirring for 3 hours at ambient temperature. After filtration and evaporation to dryness, the residue was chromatographed on silica (eluent: methylene chloride-ethyl ether 97-3) to obtain 145 mg of the expected product.

| NMR Spectrum (CDCl$_3$ 250 MHz ppm): | | |
|---|---|---|
| 6.89 and 6.93 | H$_5$ of thiazol and 0-C$\underline{H}\phi_2$ | |
| 5.93 | H$_7$ (J=5Hz) / H$_6$ | of the cis cephem |
| 5.15 | | (d, J=5Hz) |
| 5.63 | delta Z | (m) |
| 6.22 | | (d, J=11Hz) |
| 3.31 to 3.48 | ClC$\underline{H}_2$—CH and S—CH$_{-2}$ | |
| 7.25 to 7.35 | phenyls | |

STEP D: 7-[(E)-3-[(6R,7R)-7-[[[(Z)-[difluoromethoxy)imino]] [2-[(triphenylmethyl)amino]-4-thiazolyl]-acetamido]-2-[(diphenylmethoxy)carbonyl]-8-oxo-5-thia-1-azabicyclo[4,2,0]oct-2-en-3-yl]-2-propenyl]thieno[2,3-b]pyridinium iodide Using the procedure of Step B, 303 mg of the product of Step C in 5 ml of anhydrous acetone and 252 mg of potassium iodide were reacted to obtain 327 mg of the iodized derivative. 227 mg of thieno[2,3-b]pyridine and 2.5 ml of anhydrous acetonitrile were added and the mixture was stirred for one hour at ambient temperature, and finally evaporated to dryness. The residue was chromatographed on silica and eluted first with a methylene chloride-ethyl ether mixture (9-1), then with a methylene chloride-methanol mixture (95-5) to obtain 95 mg of the expected product.

| NMR Spectrum (CDCl$_3$ 60 MHz ppm): | | |
|---|---|---|
| 6.84 and 6.97 | H$_5$ of thiazol and —CH$\phi_2$ | |
| 6.75 | —OC$\underline{H}$F$_2$ | (t, J=72Hz) |
| 5.92 | H$_7$ | of the cis cephem |
| 5.10 | H$_6$ | |
| 6.6 | =CH—CH$_2$ | (d,t J=7 and 15Hz) |

-continued

| NMR Spectrum (CDCl₃ 60 MHz ppm): | | | |
|---|---|---|---|
| 5.66 | —CH₂N⁺ | | |
| 7.66 | H₄ of thienyl | ⎫ | (d, J=6Hz) |
| 7.81 | H₅ of thienyl | ⎬ thieno | (d, J=6Hz) |
| 8.78 | H in gamma position of N⁺ | ⎬ [2,3-b]pyridinium | (d, J=8Hz) |
| 8.02 | H in beta position of N⁺ | ⎬ ring | (m) |
| 9.94 | H in alpha position of N⁺ | ⎭ | (d, J=6Hz) |

STEP E: (6R,7R) 7-[(2-amino-4-thiazolyl)-(Z)-[difluoromethoxyimino]acetamido]-8-oxo-3-[(E)-3-[7-[thieno[2,3-b]pyridino]-1-propenyl]-5-thia-1-azabicyclo[4,2,0]oct-2-en-2-carboxylate 110 mg of the product of Step D were stirred for 15 minutes with 3.5 ml of trifluoroacetic acid with 10% of anisol and the insoluble part was filtered off. The filtrate was added dropwise directly into 35 ml of strongly stirred isopropyl ether. After centrifuging, two washings were carried out with isopropyl ether, triturating the residue and centrifuging each time. After drying under reduced pressure, 67 mg of the expected product were obtained. An HPLC was carried out on 60 mg of the product (column, lichrosorb RP 18) with water containing 20% of acetonitrile. After lyophilization, 22 mg of the expected product were obtained.

| NMR Spectrum (CDCl₃ 300 MHz ppm): | | |
|---|---|---|
| 3.67 | SCH₂—C═C | |
| 4.03 | N—O—CH₃ | (s) |
| 5.03 | H₆ | (d, J-5Hz) |
| 5.93 | H₇ (cis) | (dd, J=5Hz) |
| 5.33 | N⁺CH₂—CH═ | (d, J=7Hz) |
| 6.27 | N⁺CH₂—CH═ | (td, J=7 and 16Hz) |
| 7.16 | ═C—CH═CH—CH₂N⁺ | (d, J=16Hz) |
| 6.97 | CO₂CHPh₂ | (s) |
| 6.69 | H₅ of thiazol | (s) |
| 6.89 | NHCH | (d) |
| 7.04 | NHCPh₃ | (s) |
| 7.2 to 7.4 | CPh₃ and CHCPh₂ | (m) |
| 7.62 | H₃ of thienopyridinium | (d, J=6Hz) |
| 7.74 | H₂ of thienopyridinium | (d, J=6Hz) |
| 7.93 | H₅ of thienopyridinium | (dd, J=6 and 8Hz) |
| 8.74 | H₄ of thienopyridinium | (d, J=8Hz) |
| 9.10 | H₆ of thienopyridinium | (d, J=8Hz) |

| NMR Spectrum (DMSO 250 MHz, ppm): | | | |
|---|---|---|---|
| 6.99 | H₅ of thiazol | | |
| 7.10 | —OCHF₂ | | (t, J=72Hz) |
| 5.64 | H₇ | ⎫ of cephem | (d after exchange) |
| 5.09 | H₆ | ⎭ | |
| 7.4 | —CH═CH-delta E | | (d,t J=15Hz) |
| 5.91 | | | (d,t J=15 and 7Hz) |
| 9.22 | H in alpha position of N⁺ | ⎫ | (d) |
| 8.13 | H in beta position of N⁺ | ⎬ thieno | (t) |
| 9.05 | H in gamma position of N⁺ | ⎬ [2,3-b]pyridinium | (d) |
| 7.85 | H in alpha position of S | ⎬ ring | (d) |
| 8.28 | H in beta position of S | ⎭ | (d) |

EXAMPLE 3

(6R,7R)-7-[[(2-amino-4-thiazolyl)-[(Z)[methoxyimino]]-acetamido]-8-oxo-3-[(E)-3-[7-[thieno[2,3-b]pyridinio]-1-propenyl]-5-thia-1-azabicyclo[4,2,0]oct-2-en-2-carboxylate (internal salt)

STEP A:

7-[(E)-3-[(6R,7R)-2-[(diphenylmethoxy)carbonyl]-7--[[[(Z)-(methoxyimino)][2-[(triphenylmethyl)amino]-4-thiazolyl]acetamido]-8-oxo-5-thia-1-azabicyclo[4,2,-0]oct-2-en-3-yl]-2-propenyl]thieno-[2,3-b]pyridinium tetrafluoroborate A mixture of 1.331 g of silver tetrafluoroborate and 40 ml of methylene chloride was admixed with a mixture of 3.366 g of diphenylmethyl (6R,7R)-3-[(Z)-3-chloro-1-propenyl]-7-[[[(Z)-(methoxyimino)][2-[(triphenylmethyl)amino]-4-thiazolylyl]acetamido]-8-oxo-5-thia-1-azabicyclo[4,2,0]oct-2-en-2-carboxylate, 38 ml of methylene chloride and 1.05 ml of thieno[2,3-b]pyridine The mixture stood for 3 hours and 20 minutes at 20° C. and was filtered. The solvent was evaporated and the residue was chromatographed over silica. Elution with methylene chloride and then with mixtures of methylene chloride and methanol containing 2,4,6 and 8% of methanol yielded 2.004 g of the expected product.

STEP B: (6R,7R)-7-[[(2-amino-4-thiazolyl) [(Z)[methoxyimino]]acetamido]-8-oxo-3-[(E)-3-[7-[thieno[2,3-b]pyridinio]-1-propenyl]-5-thia-1-azabicyclo[4,2,0]oct-2-en-2-carboxylate (internal salt)

The product of Step A dissolved in 27 ml of formic acid with 33% of water was placed in a bath at 70° C. for one hour and then the mixture was evaporated to dryness. The residue was taken up by a mixture of ethanol and water and then the mixture was evaporated to dryness. The residue was triturated with ether and filtered. The product was dissolved in 2.5 ml of a 1M aqueous solution of triethylamine carbonate and 2.5 ml of acetonitrile. An HPLC was carried out on the product (lichrosorb column RP 18), eluting with mixture of acetonitrile and water (5-95), (10-90), (15-85) and (20-80) to obtain 0.652 g of the expected product in lyophilized form.

| NMR Spectrum (DMSO 300 MHz ppm): | | |
|---|---|---|
| 3.82 | N—O—CH₃C | (s) |
| 5.04 | H₆ | (d, J=4.5Hz) |
| 5.59 | H₇ (cis) | (m) |
| 5.58 | N⁺CH₂—CH═ | |
| 5.87 | N⁺CH₂—CH— | (t,d) |
| 7.38 | ═C—CH═CH—CH₂N⁺ | (d, J=17Hz) |
| 6.73 | H₅ of thiazol | (s) |

-continued

| NMR Spectrum (DMSO 300 MHz ppm): | | |
|---|---|---|
| 9.37 | NHCH | (d) |
| 9.23 | H$_3$ of thienopyridinium | (d) |
| 9.06 | H$_5$ of thienopyridinium | (d) |
| 8.12 | H$_4$ of thienopyridinium | (t) |
| 7.87 | H$_6$ of thienopyridinium | (d) |
| 8.28 | H$_7$ of thienopyridinium | (d) |
| 7.23 | NH$_2$ | |

EXAMPLE 4

Injectable preparations were made up of 500 mg of 7-[(E)-3-[(6R,7R)-7-[[(2-amino-4-thiazolyl) [(Z)-(methoxyimino)]acetamido]-2-carboxy-8-oxo-5-thia-1-azabicyclo[4,2,0]oct-2-en-3-yl]-2-propenyl]thieno[2,3-b]pyridinium and sterile aqueous excipient q.s. for 5 ml.

PHARMACOLOGY STUDY

In vitro activity, dilution method in a liquid medium.

A series of tubes were prepared in which an equal quantity of sterile nutritive medium was distributed. Increasing quantities of the product under test were distributed into each tube and then each tube was seeded with a bacterial strain. After incubation for 24 or 48 hours in an incubator at 37° C., the inhibition of the growth was estimated by transillumination, which enabled the minimal inhibiting concentrations (M.I.C.), expressed in micrograms/ml to be determined. The following results were obtained.

| | MIC IN μG/ML | | | |
|---|---|---|---|---|
| Strains | Product of ex. 1 24 H | Product of ex. 2 24 H | Product of ex. 3 24 H | Product of ex. 4 24 H |
| *Staphylococcus aureus* 285 | 0.15 | 5 | 2.5 | 0.15 |
| *Staphylococcus aureus* Exp. n° 54 146 | 0.3 | 5 | 2.5 | 0.3 |
| *Streptococcus pyogenes* A 561 | ≦0.01 | ≦0.01 | ≦0.01 | ≦0.01 |
| *Streptococcus pyogenes* 77 A | ≦0.01 | ≦0.01 | ≦0.01 | ≦0.01 |
| *Escherichia Coli* UC 1894 | ≦0.01 | 0.04 | 0.08 | ≦0.01 |
| *Escherichia Coli* O 75 | 0.02 | 1.2 | 0.3 | 0.02 |
| *Escherichia Coli* T E M | 0.04 | 0.6 | 0.6 | 0.08 |
| *Escherichia Coli* 1507 E | 0.01 | 0.15 | 0.04 | 0.01 |
| *Escherichia Coli* DC 0 | 0.04 | 2.5 | 1.2 | 0.04 |
| *Escherichia Coli* DC 2 | 0.01 | 0.6 | 0.08 | 0.01 |
| *Salmonella typhimurium* MZ 11 | 0.04 | 0.3 | 0.3 | 0.04 |
| *Kiebsiella pneumoniae* Exp. 52 145 | 0.08 | 0.6 | 1.2 | 0.15 |
| *Kiebsiella aerogenes* 1 522 E | 0.15 | 0.6 | 0.6 | 0.08 |
| *Enterobacter cloacae* 1 321 E | 0.04 | 0.3 | 0.6 | 0.04 |
| *Serratia RG* 2 532 | 0.15 | 10 | 5 | 0.15 |
| *Proteus mirabilis* (indol-) A 235 | 0.04 | 0.08 | 0.04 | 0.02 |
| *Proteus vulgaris* (indol) A 232 | 0.3 | 0.3 | 0.2 | 0.04 |
| *Providencia* Du 48 | 0.3 | 2.5 | 1.2 | 0.6 |
| *Pseudomonas aeruginosa* 1771 m | 0.6 | 1.2 | 2.5 | 0.0 |

Various modifications of the products and methods of the invention may be made without departing from the spirit or scope thereof and it is to be understood that the invention is intended to be limited only as defined in the appended claims.

What we claim is:

1. A compound selected from the group consisting of a syn isomer of a compound of the formula

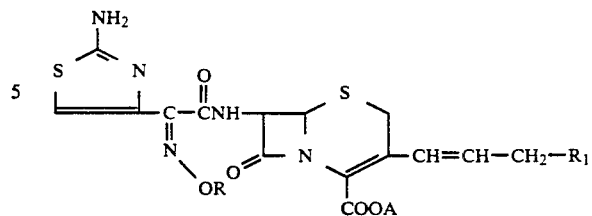

wherein R is selected from the group consisting of hydrogen, alkyl of 1 to 6 carbon atoms, alkenyl and alkynyl of 2 to 6 carbon atoms and cycloalkyl of 3 to 6 carbon atoms, all optionally substituted with at least one member of the group consisting of optionally esterified or salified carboxy, alkoxy carbonyl, carbamoyl, dimethylcarbamoyl, amino, alkylamino, dialkylamino, halogen, alkoxy and alkylthio of 1 to 4 carbon atoms, phenyl, phenylthio, tetrazolyl, tetraazolylthio and thiadiazolylthio optionally substituted by methyl, R$_1$ is selected from the group consisting of

[structures of thienopyridinium groups]

[additional structures]

A is selected from the group consisting of hydrogen, alkali metal, alkaline earth metal, magnesium, —NH$_4$ and an organic amine or A is selected from the group consisting of the residue of an easily cleavable ester group or —COOA is —COO$^-$ and the wavy line indicates —CH$_2$—R$_2$ is in the E or Z position and their non-toxic, pharmaceutically acceptable acid addition salts.

2. A compound of claim 1 wherein R is alkyl of 1 to 4 carbon atoms and alkyl of 1 to 4 carbon atoms substituted with at least one member of the group consisting of halogen, amino, carboxy, salified carboxy and esterified carboxy.

3. The compounds of claim 1 wherein $R_1$ is

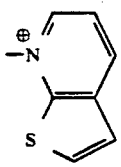

4. A compound of claim 1 selected from the group consisting of 7-[E-3-(6R,7R)-7-[(2-amino-4-thiazoyl)-[2-methoxyimino]-acetamido]-2-carboxy-8-oxo-5-thia-1-azabicyclo[4,2,0]oct-2-en-3-yl]-2-propenyl]-thieno[2,3,-b]pyridinium and its alkali metal, alkaline earth metal, magnesium, ammonium and organic amine salts, its acid form, internal salt form and easily cleavable esters.

5. A compound of claim 1 selected from the group consisting of 7-[E-3-[(6R,7R)-7-[2-amino-4-thiazolyl)--[2-difluoromethoxyimino[-acetamido]-2-carboxy-8-oxo-5-thia-1-azabicyclo[4,2,0]oct-2-en-3-yl]-2-propenyl]-thieno[2,3-b]pyridinium and its alkali metal, alkaline earth metal, magnesium, ammonium and organic amine salts, its acid form, internal salt form and easily cleavable esters.

6. A syn isomer of the formula

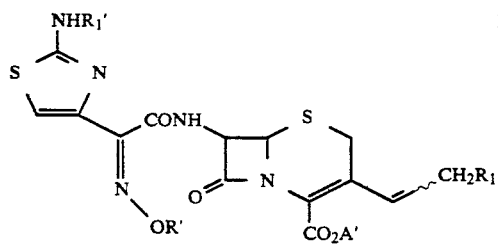

III wherein $R_1'$ is an amino protective group, A' is hydrogen or an easily removable ester group, R' is a hydroxyl protective group or R as defined in claim 1 and $R_1$ is as defined in claim 1.

7. An antibacterial composition comprising an antibacterially effective amount of at least one compound of claim 1 and an inert pharmaceutical carrier.

8. A composition of claim 7 wherein R is alkyl of 1 to 4 carbon atoms and alkyl of 1 to 4 carbon atoms substituted with at least one member of the group consisting of halogen, amino, carboxy, salified carboxy and esterified carboxy.

9. A composition of claim 7 wherein $R_1$ is

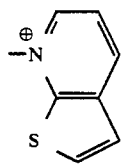

10. A composition of claim 7 wherein the active compound is selected from the group consisting of 7-[E-3-(6R,7R)-7-[(2-amino-4-thiazolyl)-[2-methoxyimino]acetamido]-2-carboxy-8-oxo-5-thia-1-azabicyclo[4,2,0]oct-2-en-3yl]-2-propenyl]-thieno[2,3-b]pyridinium and its alkali metal, alkaline earth metal, magnesium, ammonium and organic amine salts, its acid form, internal salt form and easily cleavable esters.

11. A composition of claim 7 wherein the active compound is selected from the group selected from the group consisting of 7-[E-3-[(6R,7R)-7-[2-amino-4-thiazolyl)-[2-difluoromethoxyimino]-acetamido]-2-carboxy-8-oxo-5-thia-1-azabicyclo[4,2,0]oct-2-en-3-yl]-2-propenyl]-thieno[2,3-b]pyridinium and its alkali metal, alkaline earth metal, magnesium, ammonium and organic amine salts, its acid form, internal salt form and easily cleavable esters.

12. A method of combatting bacterial infections in warm-blooded animals comprising administering to warm-blooded animals an antibacterially effective amount of at least one compound of claim 1.

13. A method of claim 12 wherein R is alkyl of 1 to 4 carbon atoms and alkyl of 1 to 4 carbon atoms substituted with at least one member of the group consisting of halogen, amino, carboxy, salified carboxy and esterified carboxy.

14. A method of claim 12 wherein $R_1$ is

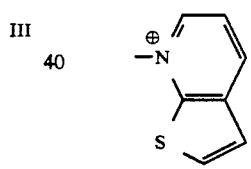

15. A method of claim 12 wherein the active compound is selected from the group consisting of 7-[E-3-(6R,7R)-7-[(2-amino-4-thiazoyl)-[2-methoxyimino]acetamido]-2-carboxy-8-oxo-5-thia-1-azabicyclo[4,2,0]oct-2-en-3-yl]-2-propenyl]-thieno[2,3-b]pyridinium and its alkali metal, alkaline earth metal, magnesium, ammonium and organic amine salts, its acid form, internal salt form and easily cleavable esters.

16. A method of claim 12 wherein the active compound is selected from the group selected from the group consisting of 7-[E-3-[(6R,7R)-7-[2-amino-4-thiazolyl)-[2-difluoromethoxyimino]-acetamido]-2-carboxy-8-oxo-5-thia-1-azabicyclo[4,2,0]oct-2-en-3-yl]-2-propenyl]-thieno[2,3-b]pyridinium and its alkali metal, alkaline earth metal, magnesium, ammonium and organic amine salts, its acid form, internal salt form and easily cleavable esters.

* * * * *